United States Patent [19]

Freeman et al.

[11] 4,086,916

[45] May 2, 1978

[54] CARDIAC MONITOR WRISTWATCH

[75] Inventors: Henry J. Freeman, Miami Beach; John M. Dinwiddie, Tamarac, both of Fla.

[73] Assignee: Joseph J. Cayre, New York, N.Y.

[21] Appl. No.: 614,898

[22] Filed: Sep. 19, 1975

[51] Int. Cl.² .............................................. A61B 5/02
[52] U.S. Cl. .......................... 128/2.05 T; 128/2.05 Z; 128/24 A
[58] Field of Search ............. 128/2 V, 2.05 E, 2.05 F, 128/2.05 P, 2.05 R, 2.05 T, 2.05 Z, 2.06 F, 2.06 R, 24 A; 58/152 B

[56] References Cited

U.S. PATENT DOCUMENTS

| | | | |
|---|---|---|---|
| 2,854,968 | 10/1958 | Wright | 128/2.05 P |
| 3,057,188 | 10/1962 | Henry | 73/67.7 |
| 3,444,726 | 5/1969 | Young et al. | 73/67.7 |
| 3,587,561 | 6/1971 | Zledonis | 128/2.05 Z |
| 3,608,545 | 9/1971 | Novack et al. | 128/2.06 F |
| 3,732,532 | 5/1973 | Flaherty | 128/2.05 Z |
| 3,742,937 | 7/1973 | Manual et al. | 128/2.05 T |
| 3,766,908 | 10/1973 | Haynes | 128/2.05 P |
| 3,807,388 | 4/1974 | Orr et al. | 128/2.05 T |
| 3,859,984 | 1/1975 | Langley | 128/2.05 Z |
| 3,948,250 | 4/1976 | Weisman | 128/2.05 T |

FOREIGN PATENT DOCUMENTS 2,219,045 10/1973 Germany ..................... 128/2.05 T

*Primary Examiner*—William E. Kamm
*Attorney, Agent, or Firm*—Berman, Aisenberg & Platt

[57] ABSTRACT

A cardiac monitoring system easily incorporated into existing electronic digital wristwatches. The self-contained unit monitors the arterial pulse rate by means of a pair of highly directional ultrasonic transducers positioned in a special mounting in the wrist band of the watch. This special mounting also includes an integrated circuit which contains the transmitter and receiver-detector electronics for connection to the transducers. The output signal from the receiver in the special mount is fed via a shielded cable in the wrist band to the processing electronics physically located within the face mounting of the watch. The processing electronics monitors the user's pulse rate and provides a digital output indication thereof if it exceeds pre-established upper and lower threshold limits. The processing circuitry also includes means for detecting an erratic heartbeat, such as a missing pulse or other irregularities, and provides an output alarm indication, both audio and visual, when such is detected. The unit is entirely self-contained and utilizes the wristwatch's standard battery power supply. External select switches are preferably provided for selection of either a time or pulse rate readout.

37 Claims, 9 Drawing Figures

CARDIAC MONITOR WRISTWATCH

BACKGROUND OF THE INVENTION

1. Field of the Invention

The present invention is related to medical diagnostic equipment and, more particularly, is directed towards a self-contained cardiac monitor which is adapted to be incorporated into a standard electronic digital wristwatch to perform concurrently therewith.

2. Description of the Prior Art

Much of the heart research being conducted today is directed toward the many clinical aspects of cardiac disease. That is, such research is directed toward uncovering information that will lead to lowering the risk of heart attacks, surgical correction of heart defects and abnormalities, and restoration of the heart patient to an active life.

In contrast, and unfortunately, very little attention in research has been paid toward the vital aspects of early detection and management of heart malfunction and disease. If a convenient and simple early detection and warning system of impending heart disease could be developed and were widely utilized, it would lead in most cases to early treatment which could prevent or delay progress of the condition.

For example, one of the most prevalent heart diseases is an outgrowth of a condition known as hypertension. Factors such as excitement, fear, frustration, and the like, all affect hypertension in varying degrees. If the onset of hypertension could be simply and accurately determined by the individual at any time, appropriate corrective action may be taken before the damage is done.

In that regard, it is important in the development of any useful cardiac monitoring system that it be enabled to respond rapidly to a sensed change in the individual's cardiac characteristics. Obviously, a system with a slow response, i.e., one which fails to notify the user at the onset of the condition, is of extremely little value.

Another factor of great importance to consider in designing and developing a suitable cardiac monitor is that it be convenient to utilize. This requirement is often translated into requirements that the device be portable, rugged, convenient, and relatively inexpensive to manufacture. Further, such a device, if it is to be utilized to maximum value, must be always in a state of readiness to detect the onset of any irregularity or variation. Thus, it must be incorporated into a device which is readily and unobtrusively worn by the individual user or patient.

Naturally, in such a cardiac monitor, a suitable indication or alarm must be given upon the detection of a malfunction or irregularity so as to alert the individual user thereof.

Prior art patents of which we are aware in this field include: Manuel et al. U.S. Pat. No. 3,838,684; Greenwood U.S. Pat. No. 3,717,140; Orr et al. U.S. Pat. No. 3,807,388; and Hokanson U.S. Pat. No. 3,777,740. Each of the foregoing patents describe cardiac monitoring devices which incorporate various techniques for monitoring the pulse or heartbeat. For example, the Manuel et al, Greenwood, and Orr et al devices utilize pressure sensitive transducers for picking up the pulse beat.

Another technique utilized in cardiac monitoring systems utilizes photo-optic transducers. Such transducers are not as sensitive to noise movement as are the pressure sensitive devices discussed above, although they are still subject to receiving false pulses. However, the basic disadvantage of utilizing photo-optic transducers as the pulse pick-up system lies in that extensive applied pressure is required in order to develop correct readings from the wrist of the user. While photo-optic devices are widely used with respect to an individual's fingers, such a device would be unduly obtrusive and not readily worn continuously. In order to render such photo-optic transducers amenable to wrist-worn devices, therefore, a special wrist restraint device must be developed and utilized. Additionally, photo-optic transducers require excessive current drain that leads to short battery lifetimes and concomitant high expense.

Since the design of the pulse pick-up system is undoubtedly critical to the operability and accuracy of a working cardiac monitor, several additional techniques were investigated. For example, microphone transducers were found to produce as much noise as the pressure sensitive transducers and were therefore rejected. Microwave transmission and detection can result in a danger to the health of the patient resulting from accumulative radiation. Further, there is a possibility of deleterious interaction of the microwave with other cardiac equipment, such as the widely used Pacemaker. Thus, microwave transmission and detection was considered and rejected. Finally, capacitive detection was attempted but was found to have an accuracy dependent upon changes in temperature and humidity which therefore led to the rejection of this type of pulse pick-up system.

SUMMARY OF THE INVENTION

It is therefore a primary object of the present invention to provide a cardiac monitoring system capable of early detection of heart malfunctions and which provides an alert system to notify the individual user of a potential problem.

Another object of the present invention is to provide a cardiac monitoring device which is convenient to utilize, relatively inexpensive, easily incorporated into existing electronic devices, and which may be continually worn by the patient while giving no outward appearance of a medical device.

An additional object of the present invention is to provide a cardiac monitor which may be incorporated into existing electronic wristwatches which utilize digital readouts.

A still further object of the present invention is to provide an electronic cardiac monitor wristwatch which rapidly responds to any detected irregularity to warn the individual user at the onset of such irregularity both visually and audibly.

A still further object of the present invention is to provide a novel and unique cardiac wristwatch monitor incorporable into existing solid state electronic digital wristwatches which may alternately, at the desire of the user, display the time of day or pulse rate.

Another object of the present invention is to provide a cardiac wristwatch monitor which, in addition to monitoring the individual's pulse rate, provides an output alarm indication upon the detection of a missed or otherwise erratic heartbeat.

A still further object of the present invention is to provide a cardiac monitoring wristwatch which utilizes a highly sensitive yet noise resistant pulse pick-up system for monitoring the pulse beat from the radial artery in the wrist of the user.

A still further object of the present invention is to provide a cardiac monitor wristwatch which has high noise rejection, does not interfere in any other respects with the health of the patient, is not responsive to excessive changes in temperature and humidity, and which may be powered by the existing miniature battery utilized in digital electronic wristwatches.

The foregoing and other objects are attained in accordance with one aspect of the present invention through the provision of a cardiac monitoring system is an electronic wristwatch. The wristwatch generally includes a face portion having contained therein electronic timing circuitry including a digital readout, and a wrist strap portion which secures the face portion about the wrist of the wearer. Mounted in the wrist strap portion, preferably adjacent the radial artery in the wrist of the user, are transmitter and receiver means in the preferable form of two highly directional ultrasonic transducers for directing a wave towards the radial artery and receiving a portion thereof reflected back towards the unit. By mixing a portion of the transmitted signal with the received signal and detecting the difference frequency, an audio analog signal is produced whose frequency is proportional to the velocity of the reflecting surface, i.e., the pulse beat.

Suitable transmitter and receiver circuits are also provided in the wrist strap portion of the unit for driving the transmitting transducer and for receiving the reflected signal, respectively. The received signal is fed to the processing electronics, located in the face portion of the wristwatch, by a shielded cable.

The received signal is processed through signal conditioning circuits in order to obtain a dc signal whose amplitude is proportional to the time duration between successive pulses of the wearer. This dc current signal is then fed into an analog-to-digital converter and other logic circuitry which provides a readable signal indicative of the pulse rate of the user.

Either the pulse rate signal or the clock circuit's regular time signal may be selected to be displayed on the wristwatch's regular light-emitting-diode display by means of an external select switch. The output from the analog-to-digital converter is also fed to a comparator circuit which delivers an output to an alarm trigger if the pulse rate falls above or below pre-established limits. The alarm trigger actuates an audible alarm and automatically causes the pulse rate to be visually displayed on the LED display.

An irregularity circuit is also provided which responds to a missing or otherwise erratic output signal from the receiver section of the transducer assembly. When triggered, the irregularity circuit actuates the audible alarm, and provides a preferably independent output indication of the irregularity condition.

In accordance with another aspect of the present invention, an ultrasonic transducer assembly is provided in which the transmitting and receiving ultrasonic transducer are mounted on a porous backing, such as foam, and encapsulated in epoxy. Upon a ceramic base is mounted an integrated circuit which contains the transmitter and receiver circuitry for the ultransonic transmitter and receiver. The i.c. mounted ceramic base is positioned adjacent the foam backing for the transducers, and an insulative coating, such as Parylene, is placed over the epoxy. The entire unit is adapted to be mounted in the wrist latch of the watch which may be then strategically positioned adjacent the radial artery of the user.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

DETAILED DESCRIPTION OF A PREFERRED EMBODIMENT

Figure 1:
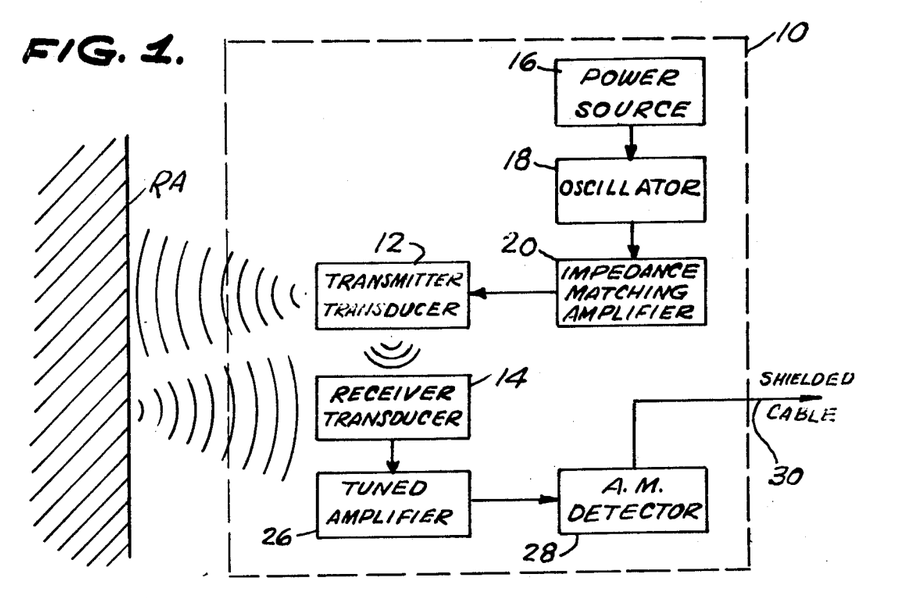
FIG. 1 is a block diagram of a preferred embodiment of the present invention in which the components illustrated are those mountable in the watch strap latch.

Referring first to FIG. 1, indicated generally by reference numeral 10 and positioned within a dotted outline are the various components which generally comprise a transmitter/receiver system for transmitting and receiving a suitable electrical signal to and from the radial artery RA of the individual wearer. The components illustrated within the dotted outline are intended to be mountable within a watch strap latch, in a manner to be described in more detail hereinbelow in connection with FIG. 2, such that the transmitter and receiver transducers are positioned most nearly adjacent the radial artery RA being monitored.

The various components which comprise the watch strap latch mounted unit 10 include a portable dc power source 16 for providing a suitable source of power to a high frequency oscillator 18. Power source 16 may conveniently be comprised of the same battery utilized to power the other components of the standard digital electronic wristwatch to be described in more detail hereinbelow.

Oscillator 18 forms the heart of the transmitter circuit which further includes a transmitter transducer 12 and an impedance matching amplifier 20 positioned between oscillator 18 and transducer 12.

Figures 2, 3, 4, 5:
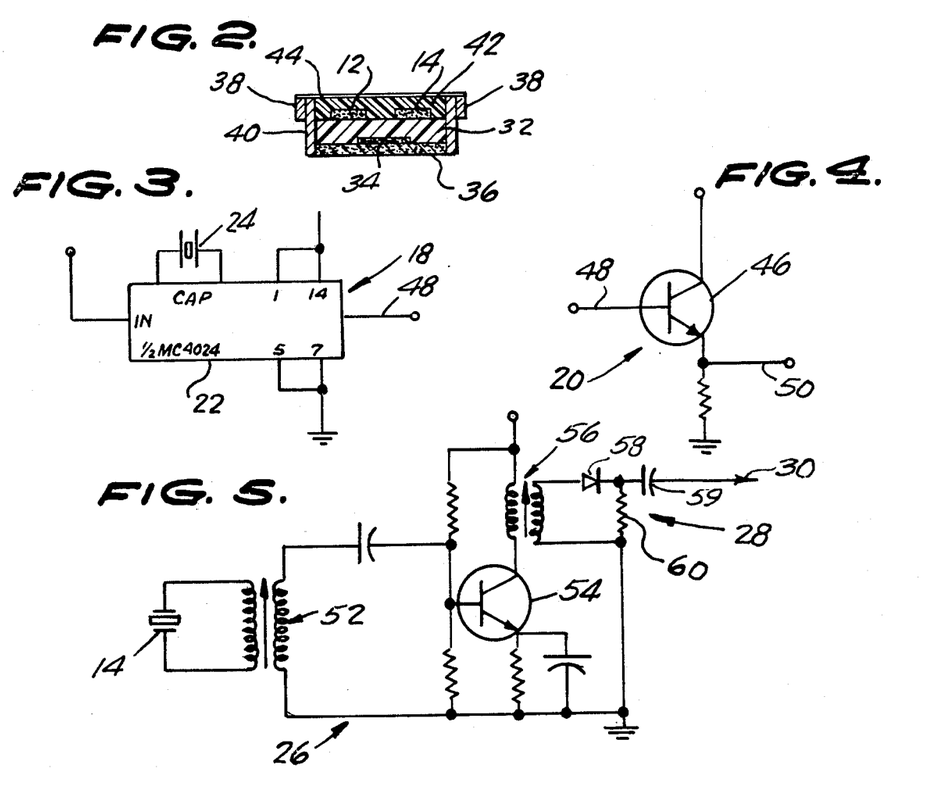
FIG. 2 is a sectional view of a preferred structural arrangement of the components illustrated in FIG. 1.
FIG. 3 is a schematic representation of a preferred integrated circuit utilized as the transmitting oscillator of the system shown in FIG. 1.
FIG. 4 is a circuit diagram illustrating a preferred configuration of an impedance matching amplifier usable in the system illustrated in FIG. 1.
FIG. 5 is a schematic diagram of a tuned amplifier and detector circuit preferably utilized in the system of FIG. 1 according to the present invention.

Referring briefly to FIG. 3, oscillator 18 is seen to preferably comprise an integrated circuit 22, such as the MC 4024, which has a 5 MHz. crystal 24 connected thereto for delivering at line 48 a 5 MHz. driving signal. The model MC 4024 is a well-known voltage-controlled astable oscillator and, as seen in FIG. 1, is coupled to transducer 12 via an impedance matching amplifier 20.

Referring briefly to FIG. 4, it is seen that impedance matching amplifier 20 may comprise a simple emitter follower transistor 46 whose base 48 is fed by the output from oscillator 18, and which delivers a signal to the transducer 12 via emitter output 50. Emitter follower transistor 46 will prevent the output from oscillator 18 from being differentiated by the transducer 12 and its associated wiring.

In selecting the type of pulse pick-ups, or transducers 12 and 14, to utilize in the system of the present invention, the factors discussed above in the BACKGROUND OF THE INVENTION were taken into careful consideration. Ideally, the desired pick-up should be able to convert the pulse detected from radial artery RA into an electrical signal without detecting extraneous interference resulting from body movement, outside electrical sources, or the like. For the preferred embodiment of the present invention, it was decided that a highly directional ultrasonic transmitter 12 and receiver transducer 14 designed expressly for the wrist best met the necessary prerequisites.

The directional capability of the transmitter transducer 12 eliminates almost all troublesome noise pulses. Further, such a directional quality utilizes far less battery current which results in an extended battery life, thereby providing a significant cost savings. The waveforms resulting from the highly directional ultransonic transducers contain only the movement of the radial artery RA which also eliminates a major source of error with prior systems. The radial artery pulse pattern results in an accurate pulse reading, requires no more pressure than a watch band exerts on the wrist, and allows considerable wrist movement without causing erroneous readings.

In a best mode, the transducers 12 and 14 are each comprised of a lead zirconate-lead titanate piezoelectric crystal. The crystal which comprises ultrasonic transducer 12 is energized by a signal from the, for example, 5 MHz. oscillator 18. The signal from oscillator 18 causes crystal 12 to expand and contract to thereby set up pressure or sound waves which are transmitted towards the radial artery RA. When this highly directional wave passes from one medium to another in the body, a portion is reflected back to the receiver transducer/crystal 14 which generates an electrical signal in response thereto. If the surface from which the transmitted wave is reflected is moving away from the transducers, the frequency of the electrical signal generated by transducer/crystal 14 will be lower than that of the signal emitted by transducer 12. Likewise, if the reflecting surface is moving toward the tranducers, the frequency of the signal generated by receiver transducer 14 will be higher than that of the signal transmitted by transducer/crystal 12. Therefore, by mixing a portion of the transmitted signal with the received signal and detecting the difference in frequency, the resultant frequency of the signal will be in the audio range and will also be proportional to the velocity of the reflecting surface RA.

Thus, the theory of operation relies upon the creation of a Doppler shifted signal resulting from ultrasonic waves emitted by transmitter 12 and reflected by the blood streaming through the vessel. As a result of the Doppler effect, the frequency of the received signal will be varied by the speed and direction of the blood flowing through the vessels, and is heterodyned to produce a usable electrical impulse.

The reflected signal is mixed with a portion of the transmitted signal in receiver transducer 14, which generates an electrical signal proportional to the difference or Doppler frequency. The output of transducer 14 is fed first to a tuned amplifier 26, and then to an AM detector 28. From detector 28, the analog pulse rate signal is fed by means of a shielded cable 30 to the processing circuitry preferably located within the face portion of a standard digital wristwatch, as will be discussed in more detail hereinafter.

Tuned amplifier 26 and AM detector 28 are illustrated in a preferred schematic circuit diagram in FIG. 5. The voltage generated across the receiving transducer 14 is fed through an impedance matching coupling transformer 52 to an amplifying transistor 54. Amplifying transistor 54, which may, for example, comprise model 2N 708, is an NPN radio frequency transistor whose output is coupled via transformer 56 to the AM detector 28. Transformers 52 and 56 are tuned to 5 MHz., the frequency of the transmitted signal, and amplifier 54 preferably has a gain of approximately 300.

AM detector 28 preferably comprises, as is standard, a diode 58 and resistor 60. An AM detector is illustrated preferably to an FM detector inasmuch as the former provides better sensitivity and does not require alignment. Amplitude detection may be utilized since a portion of the transmitted pressure wave is directly coupled to the receiver transducer 14 at the surface of the body. The mixing of the direct wave with the reflected wave causes amplitude modulation at a frequency determined by the Doppler effect. The detected audio signal outputs along shielded cable 30 via a coupling capacitor 59.

This completes the description of the components to be preferably mounted in a portion of the wrist strap such as the watch latch adjacent the pulse rate measuring point. A side section of a preferred structural configuration of the components described hereinabove is illustrated in FIG. 2. The two transducers 12 and 14, which preferably are comprised of lead zirconate-lead titanate piezoelectric crystals as described above, are each on the order of 0.25 inches in diameter. Crystals 12 and 14 are mounted on a foam-like porous material 32 which provides an air backing. This results in maximum power conversion efficiency since most of the ultrasonic energy radiated by crystals 12 and 14 which reach the porous backing 32 will be reflected in the other direction due to the intentionally poor acoustic matching. Accordingly, most of the ultrasonic energy generated will be radiated from the top portion of the crystals as viewed in FIG. 2.

Crystals 12 and 14 are held in place on foam backing 32 by means of an epoxy 42 encased thereabout. Covering epoxy 42 is an insulative coating 44, which preferably comprises Parylene. Parylene is preferred since it provides a true conformal insulation coating. Its barrier properties, resistance to corrosives, dielectric strength, and other pertinent properties are superior and provide an excellent coating for the transducers.

On the bottom side of foam backing 32, as viewed in FIG. 2, is positioned an integrated circuit 34 which is in turn fabricated on a ceramic base 36. Integrated circuit 34 may be manufactured by any well-known technique, and may incorporate the circuitry described above with respect to FIGS. 3, 4 and 5, in order to provide the ultrasonic transmitting and receiving circuitry.

The structure described above in connection with FIG. 2 may be circumferentially encased by a metal or plastic casing 40. The components 10 may be fabricated in a sufficiently small size so as to be unobtrusively accommodated within the latch mechanism of an ordinary wristwatch strap, convenient connection points 38 being provided for the watch band. Not shown in FIG. 2 are the power supply, which may be either physically located within the watch latch 10 or, alternatively, be routed in from the face portion of the wristwatch, and the shielded cable 30 for feeding the detected signal to the processing electronics in the face of the watch. The Parylene coating 44 allows transducers 12 and 14 to vibrate freely, the assembly 10 being mounted flat against the wrist in the area of interest (adjacent the radial artery).

Figure 9:
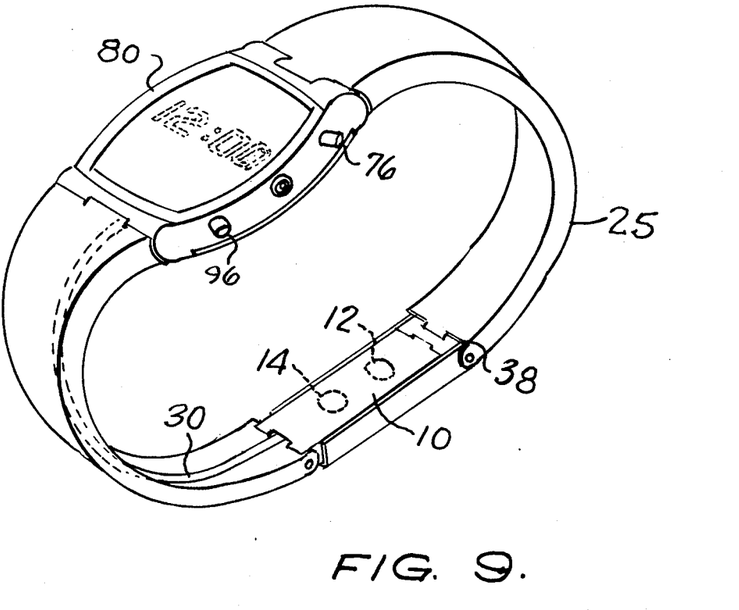
FIG. 9 is a perspective view illustrating a preferred embodiment of a digital wristwatch incorporating the present invention.

FIG. 9 is a perspective illustration of a typical digital wristwatch which incorporates the cardiac monitor of the present invention. The wristwatch of FIG. 9 includes a strap portion 25, a display or face portion 80, and a latch 10 adapted to be worn adjacent the radial artery of the user. Latch 10 has mounted therein ultrasonic transducers 12 and 14 in a manner described in more detail above in connection with FIG. 2. Latch 10 is mounted to strap 25 via connection points 38, and the shielded cable 30 is illustrated in FIG. 9 as being positioned along the inner surface of strap 25 running from latch 10 to face 80. A select switch 76 and a reset button 96 are also provided, the function of which will become more clear hereinafter.

Figure 6:
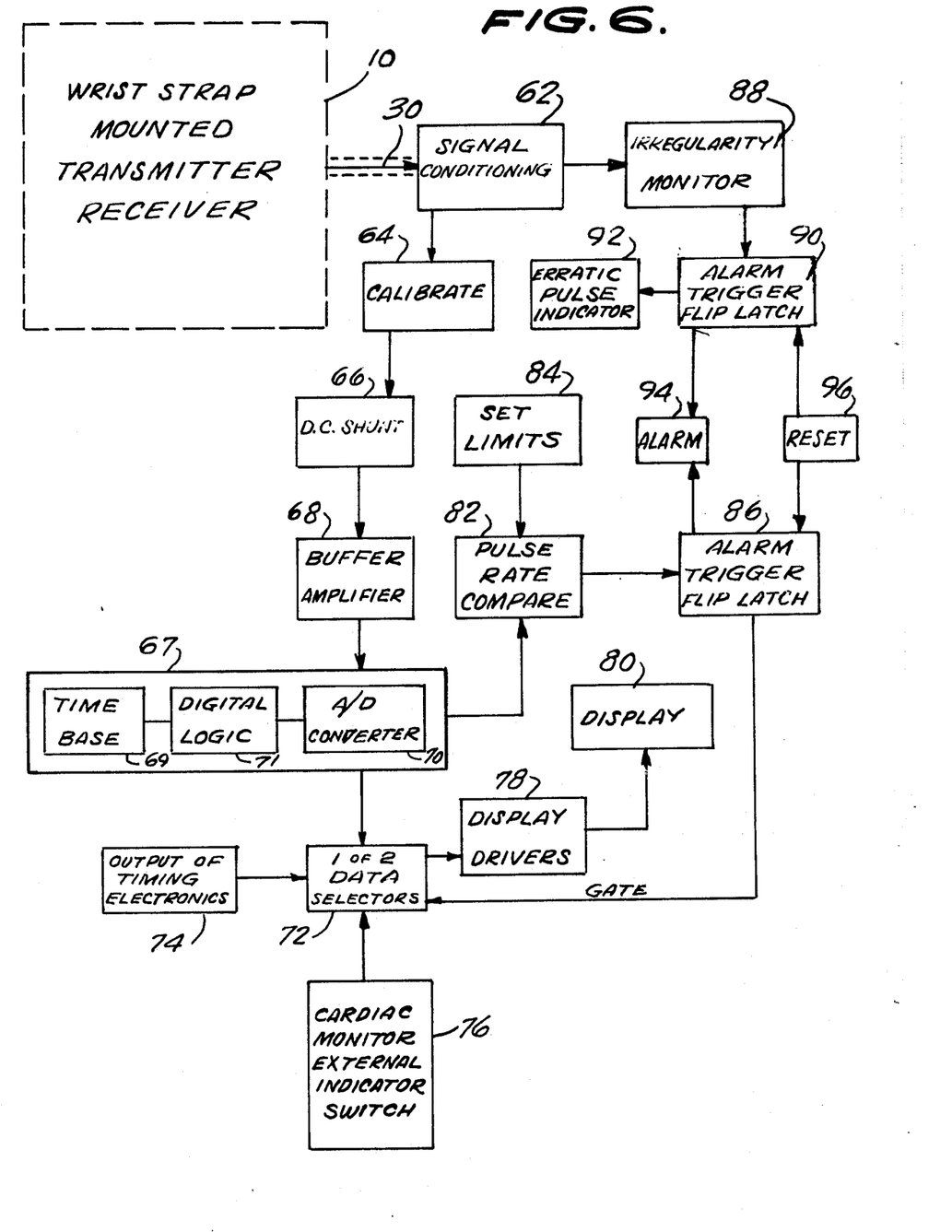
FIG. 6 is an overall block diagram illustrating the components of a preferred embodiment of the signal processing circuitry, preferably mountable in the face portion of the wristwatch, in accordance with the present invention.

Referring now to FIG. 6, a block diagram of the processing and display electronics is illustrated wherein the wrist strap mounted transmitter/receiver is again indicated generally by dotted outline 10, as is the shielded cable 30 which delivers the detected audio analog signal from the tuned amplifier and detector 26 and 28.

The analog signal from shielded cable 30 is fed through a series of signal conditioning and calibration circuits which include signal conditioning circuit 62, calibrate circuit 64, dc shunt circuit 66, and a buffer amplifier 68, all of which co-act to produce a dc current signal whose amplitude is proportional to the time duration between successive detected pulse beats.

Figure 7:
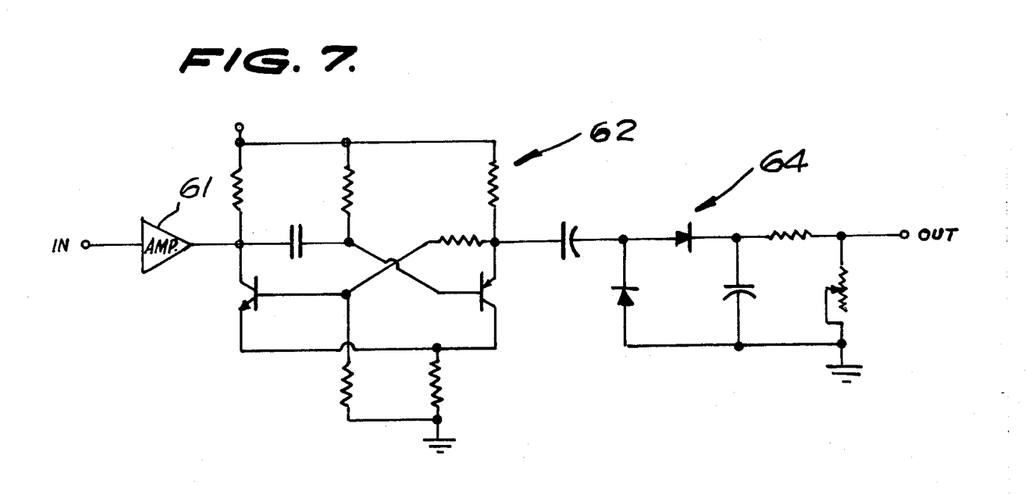
FIG. 7 is a schematic circuit diagram illustrating an embodiment of the signal conditioning and calibration circuits of the system illustrated in FIG. 6.

The signal conditioning circuit 62 and calibrate circuit 64 are shown schematically in FIG. 7. The receive signal from cable 30 is amplified by an operational amplifier 61 and then fed to a multivibrator circuit and calibrate circuit which smooth out the pulses into an approximate square current wave whose level is proportional to the time between detected pulses.

From calibrate circuit 64, the signal is sensed across a set of precision shunts 66 to develop a nominal voltage of, for example, 100 mv. at full scale. The signal is then fed through a buffer amplifier 68, which may, for example, comprise an FET follower to provide high input impedance and a gain of approximately 10 for the subsequent current measurement.

The output from buffer amplifier 68 is fed to a converter circuit 67 which, in turn, is seen to be comprised of an analog-to-digital converter 70 and associated digital logic circuitry 71 having a time base 69. The converter circuitry 67 converts the dc current input to a digital output signal which comprises a certain number of pulses per time interval that represents a value of the pulse rate (heart beats per minute). The current pulses from amplifier 68 are basically gated into counters of digital logic section 71 by time base 69. The contents of the counters are then latched, stored, and decoded, all of the foregoing being performed by conventional logic circuitry. In a best mode, converter 67 may be comprised of a single 3½ digit A/D converter LD 110 or LD 111 manufactured by Siliconix incorporated of Santa Clara, Calif.

The LD 110 and LD 111 are PMOS LSI circuit chips which constitute a complete analog-to-digital converter in two directly interfacing chips and would be particularly suitable for the instant converter 67. For example, the LD 110 integrated circuit utilizes approximately 1400 P-channel mosfets combined into logic elements for providing counting, storage, multiplexing and control operations. The decoded digital output of this chip is multiplexed and may be utilized by the remainder of the display circuitry to be explained hereinbelow.

The output of the converter circuit 67 comprises a decoded and multiplexed digital signal indicative of the individual's pulse rate. It is fed, on the one hand, to a data selector circuit 72 which selects one of two inputs for feeding to display drivers 78 and display 80. The other input to data selector 72 comprises the standard multiplexed output of the timing electronics 74 of the conventional electronic wristwatch with which the present circuitry is integrated.

We contemplate that a suitable CMOS watch chip which may be modified according to the present invention may comprise the model DF 211, manufactured by Siliconix incorporated. This watch chip provides a multiplexed four digit, seven segment LED readout. The input to data selector 72 from the watch chip 74 would be at the point of the multiplexer output.

The data selector unit 72, in a preferred mode, may comprise a type SN 54157, etc., 2-line-to-1-line data selector/multiplexer as manufactured by Texas Instruments, Inc. Such a data selector selects either the output from converter 67 or the output from clock circuit 74 to be fed to and displayed upon display 80, which preferably comprises a light-emitting-diode display, as is conventional.

A cardiac monitor external indicate switch 76 provides a manually operable externally located selector by means of which the data selector 72 can be caused to select the output from converter 67 to be fed to display 80 to read the individual's pulse rate. Another input to the data selector 72 which causes automatic output of the individual's pulse rate is received from an alarm trigger 86.

Alarm trigger 86 is activated in the following manner. The output from converter 67, which is in binary coded decimal form, is fed into a pulse rate compare circuit 82. The other input to the pulse rate compare circuit is from a standard reference 84 which also feeds to compare circuit 82 upper and lower limits in BCD form. Should the input from circuit 67 exceed the limits fed by circuit 84, compare circuit 82 will provide an output to alarm trigger 86.

Alarm trigger 86, upon receipt of a signal from compare circuit 82, will gate an output to data selector 72 to cause the pulse rate to be automatically selected and displayed on display 80. Further, alarm trigger 86, which may simply comprise a bistable flip-flop, sets an audible alarm 94 for alerting the individual of the unusual increase or decrease in his pulse rate. Alarm 94 should be loud enough to awaken an individual from sleep, but not so loud as to seriously frighten an individual who may have a history of cardiac problems.

Alarm 94 remains on until a reset button 96 is actuated to reset alarm trigger flip latch 86.

The remaining primary function of the present inventive cardiac monitor, that of providing an alarm upon the detection of abnormalities or irregularities in the rate of the heart beat, is provided by the following circuitry. The irregularity monitor 88 is also connected to receive the output from the tuned amplifier-AM detector of the transmitter/receiver 10. One function of irregularity monitor 88 is to provide an output to alarm trigger flip latch 90 upon the sensing thereby of a missing pulse in the periodic pulse train normally received by cable 30.

Figure 8:
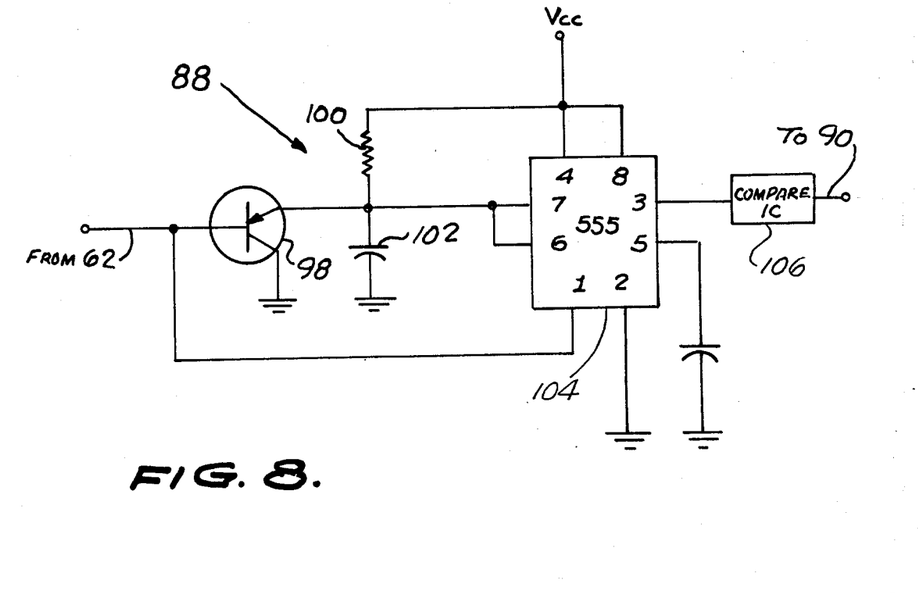
FIG. 8 is a schematic circuit diagram illustrating a preferred configuration for the irregularity monitor of the system shown in FIG. 6.

Referring now to FIG. 8, the irregularity monitor 88 is shown in more detail as comprising an input transistor 98, a timing integrated circuit 104, and a compare integrated circuit 106. Input transistor 98 receives a suitably conditioned signal from signal conditioner circuit 62 and triggers the timing cycle of timer 104. In operation, the timing cycle of timer 104 is reset continuously by each pulse in the incoming signal. If there is no missing pulse in the incoming signal, timer 104 will output a constant level signal. However, a single missing pulse in the input will permit the timing cycle of timer 104 to be completed with a resultant change in its output level. The zero compare circuit 106 will send a signal to alarm trigger flip latch 90. Resistor 100 and capacitor 102 are selected to determine the maximum time allowable between incoming pulses for triggering the timer 104. In a preferred mode, timer 104 comprises an integrated circuit model 555 and is configured as shown in FIG. 8.

Referring back to FIG. 6, the output from the irregularity monitor 88 triggers a second alarm trigger flip latch 90 which, in turn, sounds the audible alarm 94. Alarm trigger 90 also enables an erratic pulse indicator 92 which is in the form of a supplementary visual display, such as a light emitting diode, in order to provide a visual indication of the detected irregularity. Reset button 96 may also be connected so as to reset alarm trigger flip latch 90 as well.

It is seen that we have provided by virtue of the foregoing an extremely compact, simple, and inexpensive cardiac monitoring function which may be incorporated into presently existing electronic digital wristwatches. The ultrasonic pick-up technique incorporated into the design of the monitor does not have any deleterious cumulative effect on the human body and thus, the cardiac monitor may be permanently worn by an individual with no ill effect, provided that the output intensity of the ultrasonic signal is kept below approximately 1/50th of a watt per square centimeter, a non-limiting design consideration. By virtue of the device of the present invention, an individual may be apprised early in the stages of serious cardiac diseases caused by, for example, hypertension, and may seek suitable professional medical care in time to avoid serious damage to the heart. It is envisioned that the electronic technique of Large Scale Integration be employed for compressing the extensive amount of electronics into existing digital watches. By utilizing highly directional ultrasonic transmitters and receivers, extraneous noise can be avoided with extremely good sensitivity and detection.

Obviously, numerous modifications and variations of the present invention are possible in light of the above teachings. It is therefore to be understood that within the scope of the appended claims, the invention may be practiced otherwise than as specifically described herein.

We claim as our invention:

1. In an electronic wristwatch which includes a face portion having timing circuitry mounted therein which includes a digital readout of time, and a wrist strap portion for securing said face portion about the wrist of the wearer, a cardiac monitoring improvement thereto which comprises:
   means mounted in said wrist strap portion for transmitting a signal towards the radial artery of the wearer and means mounted in said wrist strap portion for receiving the signal reflected therefrom;
   means mounted in said wrist strap portion which is responsive to said transmitted and received signals for producing an analog signal proportional to the relative movement of said artery;
   means mounted in said face portion for converting said analog signal to a digital signal indicative of the pulse rate of the wearer; and
   means connected to said timing circuitry of said electronic wristwatch for selectively displaying said pulse rate on said digital readout;
   wherein said transmitting means and said receiving means each comprise an ultrasonic transducer;
   wherein said transmitting means further comprises a crystal-controlled oscillator for driving the transmitting ultrasonic transducer; and
   further comprising amplifier means connected between said oscillator and said transmitting ultrasonic transducer for matching the respective impedances thereof.

2. The cardiac monitor electronic wristwatch as set forth in claim 1, wherein said digital readout comprises a light emitting diode display.

3. The cardiac monitor electronic wristwatch as set forth in claim 1, further comprising means connecting said wrist strap portion mounted means to said face portion mounted means for connecting said analog signal therebetween.

4. The cardiac monitor electronic wristwatch as set forth in claim 3, wherein said connecting means comprises a shielded cable.

5. The cardiac monitor electronic wristwatch as set forth in claim 1, wherein said crystal-controlled oscillator comprises a 5 Megahertz oscillator.

6. The cardiac monitor electronic wristwatch as set forth in claim 1, wherein said impedance matching amplifier means comprises a transistor circuit configured as an emitter follower.

7. The cardiac monitor electronic wristwatch as set forth in claim 1, wherein said receiving means further comprises tuned amplifier means having input terminals connected across said receiving ultrasonic transducer.

8. The cardiac monitor electronic wristwatch as set forth in claim 7, wherein said receiving means further comprises AM detector means connected to receive the output from said tuned amplifier means.

9. The cardiac monitor electronic wristwatch as set forth in claim 8, wherein the input and output of said tuned amplifier means are coupled respectively to said receiving ultrasonic transducer and to said AM detector means by first and second coupling transformers, respectively.

10. The cardiac monitor electronic wristwatch as set forth in claim 9, further comprising a shielded cable connected between the output of said AM detector means and said face portion mounted means.

11. The cardiac monitor electronic wristwatch as set forth in claim 1, wherein said means mounted in said face portion further includes means for conditioning the analog signal produced by said receiving means, the output of said signal conditioning means connected to said converting means.

12. The cardiac monitor electronic wristwatch as set forth in claim 11, wherein said analog signal conditioning means includes means for producing a dc current signal whose amplitude is proportional to the time duration between successive pulses of the wearer.

13. The cardiac monitor electronic wristwatch as set forth in claim 12, wherein said dc current signal producing means comprises the electric circuit series connection of amplifier means, multivibrator means, calibrating means, shunt means and buffer amplifier means, the output of said buffer amplifier means being fed to said converting means.

14. The cardiac monitor electronic wristwatch as set forth in claim 12, wherein said converting means comprises analog-to-digital converter means for producing a series of pulses whose frequency is proportional to the input current.

15. The cardiac monitor electronic wristwatch as set forth in claim 14, wherein said converting means further comprises time base means, digital logic means connected to said time base means, said analog-to-digital converter means being connected to said digital logic means, the output of said converting means comprising a signal proportional to the pulse rate in beats per minute of the wearer.

16. The cardiac monitor electronic wristwatch as set forth in claim 15, wherein said selective display means comprises means connected to receive both said pulse rate signal and a time signal from said timing circuitry of said electronic wristwatch for selectively feeding one of said signals to said digital readout for display thereon.

17. The cardiac monitor electronic wristwatch as set forth in claim 16, further comprising manually operable switch means connected to operate said selective feeding means.

18. The cardiac monitor electronic wristwatch as set forth in claim 17, further comprising alarm activator means connected to said selective feeding means for automatically causing said pulse rate signal to be displayed upon the detection thereby of an alarm condition.

19. The cardiac monitor electronic wristwatch as set forth in claim 1, further comprising means connected to said converting means for comparing said pulse rate signal with preset upper and lower limits and for providing an output alarm signal should said pulse rate signal exceed either said upper or lower preset limit.

20. The cardiac monitor electronic wristwatch as set forth in claim 1, further comprising alarm trigger means responsive to said output alarm signal for automatically causing said displaying means to display said pulse rate.

21. The cardiac monitor electronic wristwatch as set forth in claim 20, further comprising audible alarm means activated by said alarm trigger means upon receipt thereof of said output alarm signal.

22. The cardiac monitor electronic wristwatch as set forth in claim 21, further comprising irregularity circuit means connected to receive said analog signal for providing a second output alarm signal upon the detection of an irregular pulse rate of the wearer.

23. The cardiac monitor electronic wristwatch as set forth in claim 22, wherein said irregularity circuit means comprises timer means which is reset in response to each pulse of said analog signal, the absence of one of said pulses allowing said timer means to complete its timing cycle and produce said second output alarm signal.

24. The cardiac monitor electronic wristwatch as set forth in claim 23 further comprising second alarm trigger means responsive to said second output alarm signal for actuating said audible alarm means.

25. The cardiac monitor electronic wristwatch as set forth in claim 24, further comprising visual display means mounted on the face portion of said electronic wristwatch and responsive to said second output alarm signal for providing a visual display warning in the event of a detected irregularity.

26. The cardiac monitor electronic wristwatch as set forth in claim 25, wherein said visual display means is comprised of light emitting diodes.

27. The cardiac monitor electronic wristwatch as set forth in claim 26, further comprising manually operable reset switch means for resetting said alarm trigger circuits.

28. The cardiac monitor electronic wristwatch as set forth in claim 1, further comprising irregularity circuit means connected to receive said analog signal for providing an output alarm signal upon the detection of an irregular pulse rate of the wearer.

29. The cardiac monitor electronic wristwatch as set forth in claim 28, wherein said irregularity circuit means comprises timer means which is reset in response to each pulse to said analog signal, the absence of one of said pulses allowing said timer means to complete its timing cycle and produce said output alarm signal.

30. The cardiac monitor electronic wristwatch as set forth in claim 29, further comprising alarm trigger means responsive to said output alarm signal for actuating audible alarm means.

31. The cardiac monitor electronic wristwatch as set forth in claim 30, further comprising visual display means mounted on the face portion of said electronic wristwatch and responsive to said output alarm signal for providing a visual display warning in the event of a detected irregularity.

32. The cardiac monitor electronic wristwatch as set forth in claim 31, wherein said visual display means is comprised of light emitting diodes.

33. A portable, continuously useable cardiac monitor wristwatch which comprises:
 a face which includes digital display means;
 strap means connected to said face for retaining said wristwatch about the wrist of the wearer, a portion of said strap means traversing the radial artery of the wearer;
 a first highly directional ultrasonic transducer mounted in said portion of said strap means for transmitting an ultrasonic signal towards the radial artery of the wearer;
 a second highly directional ultrasonic transducer mounted in said portion of said strap means for receiving ultrasonic signals reflected from the radial artery of the wearer;
 means responsive to said transmitted and received signals for producing an analog signal proportional to the relative movement of said artery which comprises means for producing a dc current signal whose amplitude is proportional to the time duration between successive pulses of the wearer, said dc current signal producing means including the series connection of amplifier means, multivibrator means, calibrating means, shunt means and buffer amplifier means;

means connected to receive the output of said buffer amplifier means for converting said analog signal to a digital signal indicative of the pulse rate of the wearer; and means for selectively displaying said pulse rate on said digital display means.

34. The cardiac monitor according to claim 33, wherein said portion of said strap means comprises means for latching said strap means.

35. The cardiac monitor according to claim 33, wherein said means for converting said analog signal into a digital signal is mounted in said portion of said strap means.

36. The cardiac monitor according to claim 33, wherein said means for producing an analog signal is mounted in said portion of said strap means.

37. The cardiac monitor according to claim 33, wherein said wristwatch further comprises means mounted in said face for electronically keeping track of the time of day, and means for selectively displaying said time of day on said digital display means.

* * * * *